United States Patent [19]
Oakley et al.

[11] Patent Number: 5,476,107
[45] Date of Patent: Dec. 19, 1995

[54] METHOD AND APPARATUS FOR DISINFECTING ELECTRONIC SURGICAL PROBES

[75] Inventors: Clyde G. Oakley, Englewood; Don Michal, Lakewood; Joseph V. Ranalletta, Englewood, all of Colo.

[73] Assignee: Tetrad Corporation, Englewood, Colo.

[21] Appl. No.: 152,135

[22] Filed: Nov. 16, 1993

[51] Int. Cl.[6] ............................... A61L 2/00; B08B 9/00
[52] U.S. Cl. ...................... 128/897; 128/898; 422/292
[58] Field of Search .................... 128/897, 898; 422/292–294, 296, 297, 300, 905; 206/438, 363

[56] References Cited

U.S. PATENT DOCUMENTS

| | | |
|---|---|---|
| 1,861,768 | 6/1932 | Wappler . |
| 2,546,385 | 3/1951 | Christina . |
| 2,786,245 | 3/1957 | Steinbock, Jr. . |
| 2,806,123 | 9/1957 | Steinbock, Jr. . |
| 5,120,512 | 6/1992 | Masuda . |
| 5,137,689 | 8/1992 | Cantrell . |
| 5,225,160 | 7/1993 | Sanford et al. . |
| 5,279,799 | 1/1994 | Moser ..................................... 422/292 |
| 5,288,467 | 2/1994 | Biermaier .............................. 422/293 |
| 5,310,524 | 5/1994 | Campbell et al. ...................... 422/292 |

FOREIGN PATENT DOCUMENTS

| | | | |
|---|---|---|---|
| 0072257 | 2/1983 | European Pat. Off. .............. | 422/292 |
| 2094150 | 9/1982 | United Kingdom .................. | 422/292 |

*Primary Examiner*—Angela D. Sykes
*Assistant Examiner*—Samuel Gilbert
*Attorney, Agent, or Firm*—Michael de Angeli

[57] ABSTRACT

Apparatus for disinfecting electronic probes used in surgical procedures comprises a housing for containing a disinfecting fluid and including a dummy connector for forming a sealed connection to the cable connector by which the probe is connected to associated equipment, whereby the contacts of the cable connector are protected from exposure to the disinfecting fluid.

20 Claims, 1 Drawing Sheet

METHOD AND APPARATUS FOR DISINFECTING ELECTRONIC SURGICAL PROBES

FIELD OF THE INVENTION

This invention relates to disinfection of electronic equipment used in surgical procedures. More particularly, this invention relates to techniques and apparatus for disinfecting electronic probes used in surgical procedures, wherein exposure of the contact elements of connectors of such electronic probes to the disinfecting medium is avoided.

BACKGROUND OF THE INVENTION

This invention relates to disinfection of surgical equipment, specifically electronic equipment used in surgical procedures. As used herein, the terms "sterilization" and "disinfection" are essentially equivalent, although "sterilization" generally is understood to imply the destruction of all biological material on the items sterilized, while "disinfecting" means killing all pathogenic life forms, apart from certain bacteria in spore form. The methods and apparatus of the invention are useful for both.

Increasingly, surgical procedures are performed using probes inserted into the body of a patient, as such "minimally-invasive" procedures are safer, less traumatic, and less costly than traditional open techniques. Examples of such minimally-invasive probes include endoscopic instruments for forming a visual image of a body joint, organ, or the like to be examined, as well as various types of probes for performing angioplasty and similar procedures, and ultrasonic probes for imaging body parts. Many such probes include a cable comprising a number of electric conductors for carrying signals to and from a probe head at the distal tip of the probe. This application specifically discusses ultrasonic probes, but it is to be understood that the invention claimed herein also relates to electronic probes as employed for other purposes.

In most circumstances of use, electronic probes used in surgical procedures are connected to external equipment by a multiple-conductor cable. In the example of an ultrasonic probe, such external equipment provides a drive signal to a transducer in a probe head to cause it to emit ultrasonic energy traveling into a body part to be examined. The external equipment similarly includes devices for processing return signals provided by the transducer at the probe head, responsive to detection of the ultrasonic energy after reflection within the body part to be imaged. To carry these drive and return signals, a number of conductors must be provided running along a multi-conductor cable between the external equipment and the transducer at the head of the probe. Accordingly, the complete probe comprises a probe head, including the transducer, and a multi-conductor cable, terminated by a multi-pin connector, by which the probe is connected to external equipment for providing the drive signal and processing the return signal, and also including various storage and display devices. An intermediate cable may be provided between the multi-pin connector terminating the probe cable and the external equipment.

It is essential to either sterilize the probe or to prevent contact between an unsterilized probe and the patient. There are currently available no fully satisfactory methods of sterilizing delicate surgical devices, such as probes incorporating electronic equipment.

Normal surgical disinfection and sterilization processes involve exposure of the entire probe, comprising the probe head, the cable and, preferably, the multi-pin connector terminating the cable, to a room-temperature disinfecting medium, either fluid or gas. Room-temperature disinfecting media are desirably employed for disinfection of electronic surgical equipment, as such equipment is vulnerable to elevated-temperature autoclaving or steam disinfection processes.

Disinfection of an electronic probe comprising a cable terminated by a multi-pin cable connector poses several difficulties. If the connector's contacts are exposed to and wetted by disinfecting fluids, they may corrode, interfering with their proper connection. Accordingly, a common practice is to place a fluid-tight protective cap over a ferrule in the connector housing extending around the contacts, so as to seal the contacts from the disinfecting medium. However, such caps are often lost. The cap can be retained on the cable by a flexible plastic member, chain, or the like, but this tends to be cumbersome and annoying.

If the cable connector itself is maintained outside the sterile field, the cable connector need not be disinfected. However, this requires a person outside the sterile field to handle the connection of the probe to the associated equipment (or to an intermediate cable, if used) while a surgeon or other person within the sterile field is obliged to handle the sterilized probe end.

Another possibility is to encase the probe itself in a thin rubber or plastic sheath, thus preventing the patient from being touched by a nondisinfected probe. However, this solution is not satisfactory in connection with ultrasonic probes, wherein direct connection of the transducer to the tissue to be imaged is important. This solution is also useless in connection with probes providing aspiration or irrigation, requiring one or more lumens in communication with the probe head, nor where an optical image must be formed, as the sheath would interfere with optical transmission. Further, it appears likely that in the near future even devices that are sheathed in use will be required to be disinfected.

More specifically, disinfection is commonly accomplished by immersing the probe head and cable, using a "high-level" disinfectant, such as that sold as "Cidex", in an open tray for ten to thirty minutes prior to use, while allowing the cable connector, with the contact elements exposed, to simply remain outside the tray. Sterilization is accomplished similarly, but involves a much longer period of exposure to the disinfectant, typically ten to 24 hours. Both involve the difficulties mentioned above, namely, that the connector can be damaged if accidentally exposed to the disinfectant, and that two persons are required to make the connection of the equipment to an external instrument, power supply or the like.

Alternatively, delicate electronic surgical equipment that cannot withstand high temperature sterilization can be sterilized by exposure to ethylene oxide (EtO). The internal and external surfaces of the equipment are exposed to the EtO gas, and are then evacuated as necessary. While this gas does not damage or corrode the electrical connectors used, its use has several inherent difficulties. First, EtO is toxic, such that government regulations restrict its use. EtO is also commonly mixed with freon, to reduce its explosiveness; freon is in the process of being banned. Further, EtO sterilization is very time-consuming.

More recently, there have been developed self-contained sterilization units (see U.S. Pat. No. 5,225,160 to Sanford et al) that are capable of sterilizing various sorts of equipment in a convenient and rapid fashion. In use of these units, the equipment to be sterilized is disposed in a sealable chamber, and the interior and exterior surfaces thereof are exposed to a liquid chemical sterilant, under controlled temperature and pressure conditions, followed by a controlled water rinsing step. However, this system cannot be used without exposing the entire device to be sterilized to the sterilant, and thus is not useful for sterilizing electronic instruments having unprotected connectors for connection to external devices. As noted, simply providing a cap for the connector is insufficiently reliable to solve this problem.

Therefore, it is apparent that there exists a need for an efficient and convenient method of disinfecting an electronic probe comprising a probe head connected by a multiple-conductor cable to a multi-pin connector for connection to external equipment, such that the entire probe including the connector can be disinfected simultaneously, including any lumens and internal surfaces of the probe, without exposing the contact pins of the multi-pin connector to the disinfecting medium.

The following patents relate generally to the subject of disinfection of surgical or dental equipment.

Wappler U.S. Pat. No. 1,861,768 shows a basic "fumigating" sterilizer unit, including a sealed chamber having internal gas outlets for connection to the interior of catheters and the like.

Steinbock U.S. Pat. No. 2,786,245 shows a sterilizer tray including hollow posts for holding dental handpieces upright for drainage after sterilization. The dental tray is perforated to allow it to be lowered into a sterilizing fluid or the like. A second Steinbock U.S. Pat. No. 2,806,123, is generally similar.

U.S. Pat. No. 5,120,512 to Masuda recognizes the difficulty of sterilizing a precision instrument such as a dental handpiece using steam or ethylene oxide gas, and shows a ozonating chamber for bacteriostatic purposes. Various devices may be connected to mating fittings for sterilizing their interior passages.

U.S. Pat. No. 5,137,689 to Cantrell shows a sterilizing device wherein instruments are connected by pressure fittings to receive pressurized sterilizing fluid for cleaning their internal surfaces.

U.S. Pat. No. 2,546,385 to Christina shows a custom-fitted tray for efficient receiving and cleaning of ampules for medicines and the like.

As noted above, U.S. Pat. No. 5,225,160 to Sanford et al shows a system for decontaminating and sterilizing medical instruments such as endoscopes, wherein an antimicrobial liquid may be sprayed on the exterior surface of the instrument and be supplied to the internal surfaces thereof.

As indicated above, the disinfection of an electronic probe used in surgical procedures presents a special problem not solved by the prior art patents discussed above.

OBJECTS OF THE INVENTION

It is therefore an object of the invention to provide a method and apparatus for disinfecting electronic probes used in surgical procedures.

It is a further object of the invention to provide a method and apparatus for disinfecting electronic probes and similar devices used in surgical procedures, wherein the device is connected to associated equipment by a cable terminated by a multi-pin connector, and whereby the external surfaces of the entire device, including the cable and the connector, as well as any lumens or other internal surfaces thereof, can be disinfected by exposure to a disinfecting fluid, without exposure of the contacts of the multi-pin connector to the fluid.

SUMMARY OF THE INVENTION

The above objects of the art and others which will appear as the discussion below proceeds are satisfied by the present invention, wherein an electronic probe or similar device for surgical procedures comprising a multi-pin electrical connector is disinfected in an apparatus for containing a disinfecting medium, more particularly, a disinfectant fluid. (Throughout this application, and the appended claims, "disinfection" is to be understood to include "sterilization.") Prior to exposure of the probe to the disinfectant fluid, the cable connector of the probe is connected to a dummy connector built into the apparatus for containing the disinfecting fluid. Conveniently, the dummy connector can be built into the wall or floor of a tray or chamber for containing the probe. The cable connector physically mates with the dummy connector in substantially the same manner in which the cable connector mates with a cooperating connector on associated external equipment, or on an intermediate cable. A seal is provided between the cable connector and the dummy connector, sealing the contacts of the cable connector from the disinfecting fluid. The container may then be filled with the disinfectant fluid, or the probe may be sprayed with the disinfectant fluid. Any internal surfaces or cavities of the probe will normally be in communication with the cable connector via one or more lumens running along the length of the cable; accordingly, such internal surfaces or cavities may be disinfected by supplying the disinfectant fluid to the end of the lumen at the cable connector under pressure. In this way, the entire cable assembly can be disinfected without exposing the contacts to the disinfecting medium.

BRIEF DESCRIPTION OF THE DRAWINGS

The invention will be better understood if reference is made to the accompanying drawings, in which.

DESCRIPTION OF THE PREFERRED EMBODIMENTS

As discussed above, it is an object of the invention to provide a method and apparatus for disinfecting an entire electronic probe for use in surgical procedures. Such a probe typically comprises a probe head, a cable, and a multi-pin connector terminating the cable, the cable connector being used to connect the probe to associated external equipment, either directly or through an intermediary cable. It is particularly desirable to disinfect the entire probe in a single operation while avoiding any possibility of exposing the contacts of the cable connector to the disinfecting medium.

Figure 1:
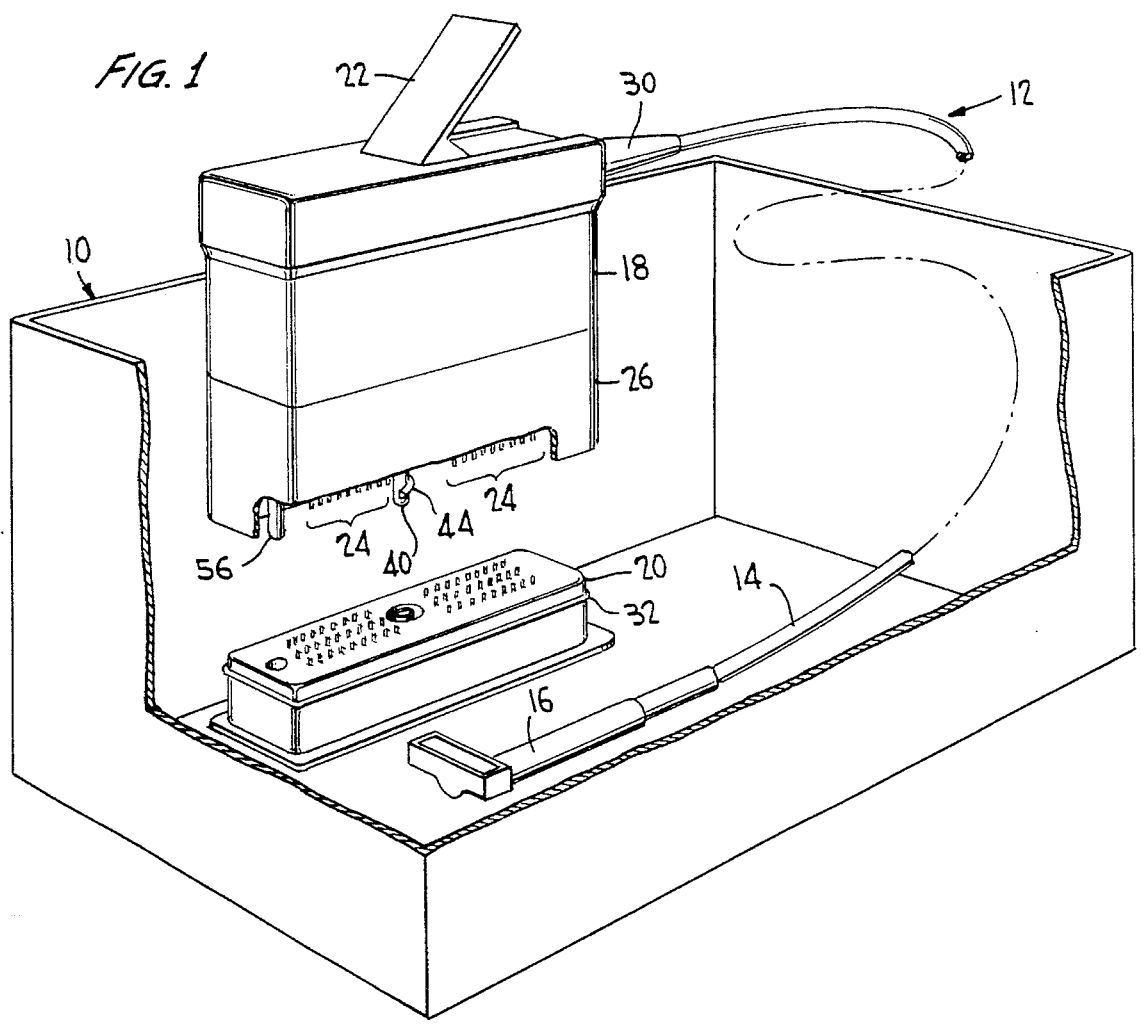
FIG. 1 shows a perspective view of a tray for containing disinfecting fluid according to the invention, and having an electronic surgical probe disposed therein for disinfection.

FIG. 1 shows a perspective view of apparatus according to the invention, including a container 10 for receiving a quantity of a disinfecting liquid. Container 10 may be part of, or may be configured to fit into, the sealable chambers of known sterilizing equipment, such as that described in the Sanford et al patent discussed above, and may be adapted to contain the probe while immersed in or sprayed with the disinfectant fluid.

As shown, an electronic probe 12 for surgical use may be disposed in container 10 for disinfection. Probe 12 may typically comprise a probe head 16, e.g., comprising a piezoelectric transducer for ultrasonic examination of body structures, or any of a wide variety of other devices for interacting in some desired way with a patient for diagnostic or therapeutic purposes. Probe 12 further comprises an elongated flexible cable 14, and a multi-pin cable connector 18 terminating cable 14. The exterior surface of probe head 16 may be integrally formed with or sealed to cable 14, preventing the disinfecting fluid from penetrating probe head 16.

In order that probe 12 may be exposed to a suitable disinfecting fluid for killing organisms on the probe, container 10 may be filled to a desired level with the disinfecting fluid covering all exposed surfaces of the probe, or the fluid may be sprayed on the probe 12. See the Sanford et al patent discussed above. According to the invention, in order to prevent the disinfecting fluid from wetting and possibly corroding the contacts 24 of connector 18, or otherwise damaging the probe by contacting the contacts, the cable connector 18 is sealingly secured to a dummy connector 20 formed in the floor of the container 10 (as shown), or in a wall thereof. Dummy connector 20 receives connector 18 in essentially the same manner as do cooperating connectors of external equipment in normal use, e.g., for supplying drive signals to the probe 12 and receiving return signals therefrom.

More specifically, cable connector 18 is received by dummy connector 20 such that the dummy connector 20 is sealed to a portion of the external housing of the cable connector 18, and exposure of the contacts of the connector 18 to the disinfecting fluid is prevented. For example, a resilient sealing member 32 may be retained by the dummy connector 20 in order to be sealed to a mating surface of a ferrule 26 surrounding the electrical contact elements 24 of the cable connector, for example, contact pins of paired contact elements adapted to receive pins of a cooperating connector. See FIG. 2.

Typically, the dummy connector 20 will physically resemble the cooperating connector on associated external equipment, or on an interconnecting cable, so that the dummy connector receives the cable connector 18 in substantially the same manner as would a cooperating connector. The term "substantially" as used in this context reflects the fact that normally it will not be necessary to provide electronic contact between the dummy connector 20 and the contacts 24 of the cable connector 18, although mating contacts might be provided in dummy connector 20; a simple electrical circuit could then be provided to permit verification of the proper positioning of cable connector 18 within dummy connector 20. The cable connector 18 may be secured in place within the dummy connector 20 by the same locking mechanism (exemplified by operating lever 22) as employed in use of the probe to secure the cable connector 18 to associated equipment, or to an intermediate cable.

Figure 2:
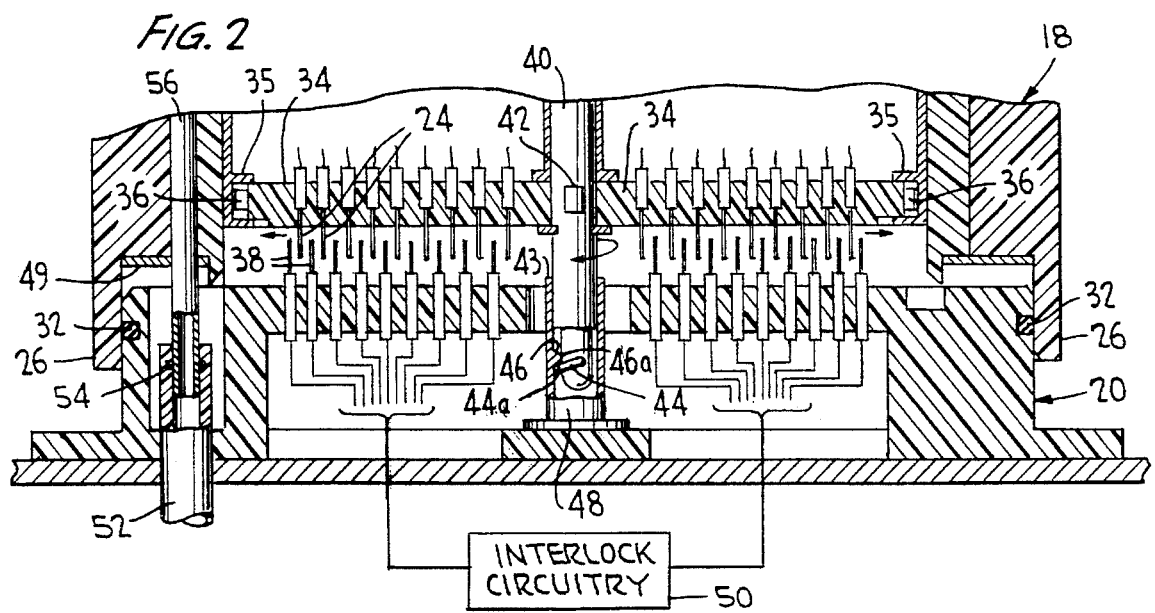
FIG. 2 shows a cross-sectional view through a cable connector and a dummy connector according to the invention, and illustrates one possible arrangement for conveniently securing the cable connector of an electronic probe to a dummy connector in a tray for containing a disinfecting fluid.

FIG. 2 shows one exemplary structure whereby a multi-pin cable connector 18 of a probe 12 may be sealed to a dummy connector 20. As shown, the cable connector 18 comprises a number of contact elements 24 within an outer ferrule 26 of the cable connector housing. The housing is sealed to a strain relief 30 (FIG. 1) for providing fluid-tight sealed connection to cable 14. The dummy connector 20 may comprise an O-ring or similar resilient sealing member 32 for engaging a mating surface of ferrule 26 and providing a fluid-tight sealed connection therewith. Thus, when the connector 18 is properly secured within dummy connector 20, the container 10 may be filled with a disinfecting fluid, immersing the probe 12, or the probe 12 may be sprayed with the fluid, without exposure of contact pins 24 thereto.

It is important to ensure that the probe connector 18 does not escape from the dummy connector 20 during the disinfection process. An exemplary structure for so doing is shown in FIG. 2, specifically suitable for use with a cable connector 18 and dummy connector 20 of the so-called zero-insertion-force (ZIF) type. In ZIF connectors of the type shown (other types of cable connectors being within the scope of the invention) the contacts 24 of the cable connector 18 are mounted in a pair of laterally-movable planar members 34. Members 34 are supported for lateral movement in channel-shaped supports 35 and are biased toward the center of the connector 18 by springs 36. In order that contacts 24 can engage the corresponding contacts of a mating connector on associated external equipment, or engage contacts 38 optionally provided as part of the dummy connector 20, members 34 are moved outwardly by rotation of an operating rod 40 to which are affixed cam lobes 42.

According to a particularly preferred embodiment of the invention, locking rod 40 is rotated by operation of an operating lever 22 pivoted about an axis perpendicular to the axis of rotation of locking rod 40, as more fully disclosed in copending application Ser. No. 08/164,578, filed Dec. 10, 1993, now U.S. Pat. No. 5,368,496. However, the present invention is equally useful in connection with cable connectors operated by conventional means.

More specifically, in a preferred embodiment, the rod 40 rotates within a bore fixed with respect to the housing of the cable connector 18. The distal tip of rod 40 fits within a tubular element 43 mounted to dummy connector 20, such that the dummy connector 20 effectively defines a tubular recess. A downwardly-extending arcuate ridge 46 extends partially around the inner surface of tubular element 43; typically, the arcuate ridge 46 defines a lower surface 46a extending around between about 90° and about 180° of the inner surface of tubular element 43. A member 44 on the distal tip of the rod 14 defines a cooperating upper surface 44a extending generally transversely outwardly from the cylindrical surface of rod 40, but "wrapped" therearound, so as to extend arcuately downwardly, again through between about 90° and about 180°. Arcuate ridge 46 and member 44 thus cooperate to form a portion of a screw thread; accordingly, if the tip of rod 40 is inserted into the tubular recess 43, such that member 44 is disposed beneath and to one side of ridge 46, and rod 40 continues to be inserted while being rotated, upper surface 44a of member 44 slides along the lower surface 46a of member 46, drawing the cable connector 18 into the dummy connector 20.

Thus, when cable connector 18 is inserted into dummy connector 20, rod 40 enters member 43. Rod 40 is then rotated, while being inserted further, such that the downwardly-curving shape of ridge 46 cooperates with the cooperating shape of member 44 to pull cable connector 18 firmly into dummy connector 20, while at the same time contacts 24 are moved laterally outwardly.

If cable connector 18 is sealed to dummy connector 20 by a resilient member mounted to one of the confronting surfaces thereof meeting along a plane perpendicular to the direction in which the cable connector 18 is inserted into the dummy connector 20, e.g., at 49, the cooperation of ridge 46 and member 44 during rotation of rod 40, pulling the connectors 18 and 20 together, compresses the resilient member therebetween, ensuring a fluid-tight connection.

Alternatively, member 44 and ridge 46 may be supplanted by or complemented with other equivalent structures, such as a pin extending transversely outwardly from rod 40, and fitting within an arcuate slot formed in the tubular member 43.

In the event the cable 14 comprises one or more interior lumens for provision of irrigation or aspiration to the vicinity of the head 16, such lumens and any interior surfaces or cavities of probe head 16 will normally also require disinfection. To this end a conduit 52 may be provided as part of the dummy connector 20. Conduit 52 comprises a second O-ring 54 for mating with a tube 56 in the cable connector 18 communicating with the lumen of the probe. Disinfecting medium supplied under pressure via conduit 52 to tube 56 will contact and disinfect all interior surfaces of the probe 12, while the disinfecting medium contacts all exterior surfaces of probe 12 while disposed in the container 10.

As shown, the dummy connector 20 may be fitted with contacts 38 connected to interlock circuitry 50, for testing whether the cable connector is properly inserted into and fixed to the dummy connector 20.

The method of disinfecting a probe comprising a multi-pin electrical connector according to the invention thus involves the steps of providing a disinfecting apparatus for receiving the probe, the apparatus being adapted to contain a quantity of a disinfecting medium and comprising a dummy connector for mating with the connector of the probe, substantially as would a cooperating connector; disposing the probe in the apparatus and inserting the connector of the probe into the dummy connector, such that a sealed connection is formed therebetween; exposing the surfaces of the probe to the disinfecting liquid, either by immersing the probe in the disinfecting fluid, or spraying it onto the probe, and allowing the fluid to remain in contact with the probe for a sufficient period of time to ensure disinfection thereof; and removing the medium and the probe from the apparatus.

Where the probe connector is a zero insertion force connector, a further step of positively urging the probe connector into the dummy connector may be performed to compress a resilient sealing member therebetween, to ensure that a suitable seal is formed and maintained therebetween.

Where the probe head comprises an internal cavity in communication with a lumen running up the cable, the method of the invention may comprise the further step of supplying disinfecting fluid to a tube connected to the lumen by way of the dummy connector, such that the internal cavity of the probe is similarly disinfected.

In the above, the probe has been described as comprising a probe head connected to an elongated flexible cable terminated by a multi-pin connector. It is also within the invention to configure the probe as a relatively short unit, having a multi-pin connector near the probe head for connection of an intermediate flexible cable. Such an intermediate cable could be disinfected according to the invention by providing first and second dummy connectors corresponding to both its cable connectors in a disinfecting apparatus, which would typically also include a third dummy connector for protecting the connector of the probe during disinfection.

While a preferred embodiment of the invention has been described, it will be understood that this is not intended as a limitation on the invention, which is more properly defined only by the following claims.

What is claimed is:

1. A method for disinfecting electronic probes used in surgical procedures, wherein said electronic probes comprise a probe head sealed to a distal end of a flexible cable, and a cable connector secured to a proximal end of said cable, said cable connector comprising a housing sealed to said cable and a plurality of contacts, said cable connector being adapted to mate in a predetermined manner with a cooperating connector comprised by associated equipment, said method comprising the steps of:

providing a disinfecting apparatus for receiving a probe to be disinfected, said apparatus being adapted to contain a disinfecting medium, and said apparatus comprising a dummy connector for receiving a cable connector of said probe, and for forming a sealed connection with a housing thereof;

disposing said probe in said apparatus;

inserting said cable connector into said dummy connector, such that a sealed connection is formed between said dummy connector and said housing, such that said contacts of said cable connector are sealed from disinfecting medium in said apparatus;

exposing substantially all external surfaces of said probe to said disinfecting medium;

allowing said medium to contact said surfaces of said probe for at least a predetermined period of time;

removing said medium from said apparatus; and removing said probe from said apparatus.

2. The method of claim 1, wherein said cable connector and said dummy connector cooperate to form a zero-insertion-force connection, and said method comprises the further step of securing said cable connector in said dummy connector, forming said sealed connection therebetween.

3. The method of claim 2, comprising the further step of compressing a resilient sealing member comprised by said dummy connector against said housing of said cable connector upon securing of said cable connector in said dummy connector, forming a seal therebetween.

4. The method of claim 1, wherein said probe comprises a lumen extending from said connector, along said cable, to said probe head, and said dummy connector comprises a conduit for mating with said lumen at said probe connector, and said method comprises the further step of supplying said disinfecting medium to said conduit.

5. Apparatus for disinfecting electronic probes used in surgical procedures, wherein said electronic probes comprise a probe head sealed to a distal end of a flexible cable, and a cable connector secured to a proximal end of said cable, said cable connector comprising a housing sealed to said cable and having a plurality of exposed contacts, said cable connector being adapted to mate with a cooperating connector connected to associated equipment such that said contacts of said cable connector abut a corresponding plurality of contacts comprised by the cooperating connector, said apparatus for disinfecting comprising means for receiving said electronic probe, said means for receiving being adapted to contain a disinfecting medium, and said means for receiving comprising a dummy connector for receiving said cable connector of said electronic probe and forming a sealed connection with said housing of said cable connector, such that said contacts of said cable connector are sealed from said disinfecting medium.

6. The apparatus of claim 5, wherein said means for receiving being adapted to contain a disinfecting medium is a container for containing a disinfecting fluid, said dummy connector being mounted under a normal level of said disinfecting fluid in said container.

7. The apparatus of claim 5, wherein said probe has at least one internal lumen formed therein, extending from a proximal opening at said cable connector, along said cable, to said head, and said dummy connector further comprises conduit means for sealingly mating with said proximal opening of said at least one lumen when said cable connector is secured in said dummy connector, and said apparatus comprises means for supplying said disinfecting medium under pressure to said conduit means, whereby said lumen may be disinfected together with any internal surfaces of said probe.

8. The apparatus of claim 5, further comprising contacts in said dummy connector for mating with the contacts of said cable connector, and interlock circuit means for determining whether said connectors are properly connected to one another.

9. In combination, an electronic probe to be disinfected and the apparatus of claim 5, said electronic probe comprising a probe head sealed to a distal end of a flexible cable, and a cable connector secured to a proximal end of said cable, said cable connector comprising a housing sealed to said cable and having a plurality of exposed contacts, wherein said cable connector and said dummy connector cooperate to form a zero-insertion-force connection, and said apparatus further comprising means for securing said cable connector with respect to said dummy connector, and a resilient sealing member between mating surfaces of said cable connector and said dummy connector, to ensure a fluid-tight sealed connection is formed therebetween.

10. The combination of claim 9 wherein said resilient sealing member is compressed between mating faces of said dummy connector and said cable connector upon securing said cable connector with respect to said dummy connector.

11. The combination of claim 10, wherein said cable connector comprises a locking rod retained in a bore formed in said cable connector and rotatable therein, and said dummy connector defines a generally tubular recess for receiving a distal tip of said locking rod, and wherein said dummy connector and said rod comprise members cooperating such that said tip of said rod may be inserted into said recess and rotated in order to secure said tip of said rod within said recess, securing said cable and dummy connectors to one another and compressing said resilient sealing member therebetween.

12. The combination of claim 11, wherein said mating cable and dummy connectors meet along a generally planar mating plane, and said resilient sealing member is compressed between mating surfaces generally parallel to said mating plane.

13. The combination of claim 11, wherein said members cooperating such that said tip of said rod may be inserted into said recess and rotated in order to secure said tip of said rod within said recess, and securing said cable and dummy connectors to one another, comprise a member extending transversely from said distal tip of said rod and means defining an arcuate surface formed in said tubular recess, for cooperating with said member extending transversely from said distal tip of said rod, said arcuate surface being shaped such that as said rod is inserted into and rotated within said recess, said member slides along said arcuate surface so as to draw said rod into said recess, securing said cable and dummy connectors to one another.

14. The combination of claim 13, wherein said member extending transversely from said distal tip of said rod defines an upper surface extending generally transversely outwardly from a cylindrical surface of said rod and extending arcuately therealong.

15. In apparatus for disinfecting electronic probes used in surgical procedures, wherein said probes comprise a probe head connected by a cable to a multi-pin cable connector for establishing electrical connection to associated equipment, said associated equipment comprising a cooperating connector for physically mating and forming electrical connection with a multi-pin cable connector of such a probe, said apparatus comprising means for containing a quantity of a disinfecting medium together with equipment to be disinfected, the improvement comprising:

a dummy connector disposed in said means for containing such that in normal use said dummy connector is exposed to said disinfecting medium, said dummy connector being adapted to physically mate with a multi-pin cable connector of a probe to be disinfected in substantially the same manner as the cooperating connector of the associated equipment, and said dummy connector being adapted to form a sealing connection with said cable connector, whereby when a cable connector is inserted into and secured to said dummy connector, the pins of said cable connector are prevented from contact with said disinfecting medium.

16. The apparatus of claim 15, wherein said means for containing a disinfecting medium is a tray for containing a disinfecting fluid, said dummy connector being mounted under a normal level of said disinfecting fluid in said tray.

17. The apparatus of claim 15, wherein said probe has at least one internal lumen formed therein, extending from a proximal orifice at said cable connector, along said cable, to said head, and said dummy connector further comprises conduit means for sealingly mating with said proximal orifice of said at least one lumen of said cable connector when said cable connector is secured in said dummy connector, and said apparatus comprises means for supplying disinfecting medium under pressure to said conduit means, whereby said lumen may be disinfected together with any internal surfaces of said probe in communication with said lumen.

18. The apparatus of claim 15, wherein said dummy connector further comprises contacts for mating with the pins of said cable connector, and interlock circuit means for determining whether said connectors are properly connected to one another.

19. In combination, an electronic probe to be disinfected and the apparatus of claim 15, said probe comprising a probe head connected by a cable to a multi-pin cable connector for establishing electrical connection to associated equipment, wherein said dummy connector comprises a resilient sealing member for forming a sealing connection with said cable connector, and said cable connector comprises means for compressing said resilient sealing member between mating surfaces of said cable connector and said dummy connector upon securing of said cable connector to said dummy connector, to ensure a fluid-tight sealed connection is formed therebetween.

20. The combination of claim 19, wherein said cable connector is adapted to cooperate with a mating connector to form a zero-insertion-force connection therebetween, and said apparatus further comprises means for simultaneously actuating means for moving the contacts of the cable connector, and securing said cable connector to said dummy connector.

* * * * *